United States Patent [19]
Lonnroth

[11] 4,050,290
[45] Sept. 27, 1977

[54] DEVICE FOR MEASURING FRICTION BETWEEN WHEEL AND SUPPORT

[76] Inventor: Börje Arne Gunnar Lönnroth, Abiskovagen 6, Vallingby, Sweden, S-162 25

[21] Appl. No.: 635,352

[22] Filed: Nov. 26, 1975

[30] Foreign Application Priority Data

Nov. 27, 1974 Sweden .............................. 7414859

[51] Int. Cl.² ............................................ G01N 19/02
[52] U.S. Cl. ....................................................... 73/9
[58] Field of Search .................... 73/9, 146; 33/203.14

[56] References Cited

U.S. PATENT DOCUMENTS 3,538,742   11/1970   Benning ..................................... 73/9

FOREIGN PATENT DOCUMENTS 789,419   8/1935   France ..................................... 73/9

Primary Examiner—Richard C. Queisser
Assistant Examiner—Joseph W. Roskos
Attorney, Agent, or Firm—Birch, Stewart, Kolasch and Birch

[57] ABSTRACT

The present invention relates to a device for measuring friction between wheels and the wheel support. The device of the present invention is such that the friction, upon movement of the wheels, results in a measurable turning moment about a line, perpendicular to the direction of movement and substantially parallel or coinciding with a line through the centers of the wheels. The moment arises and is measured on suspension means of the wheels and/or a member interconnecting them.

8 Claims, 6 Drawing Figures

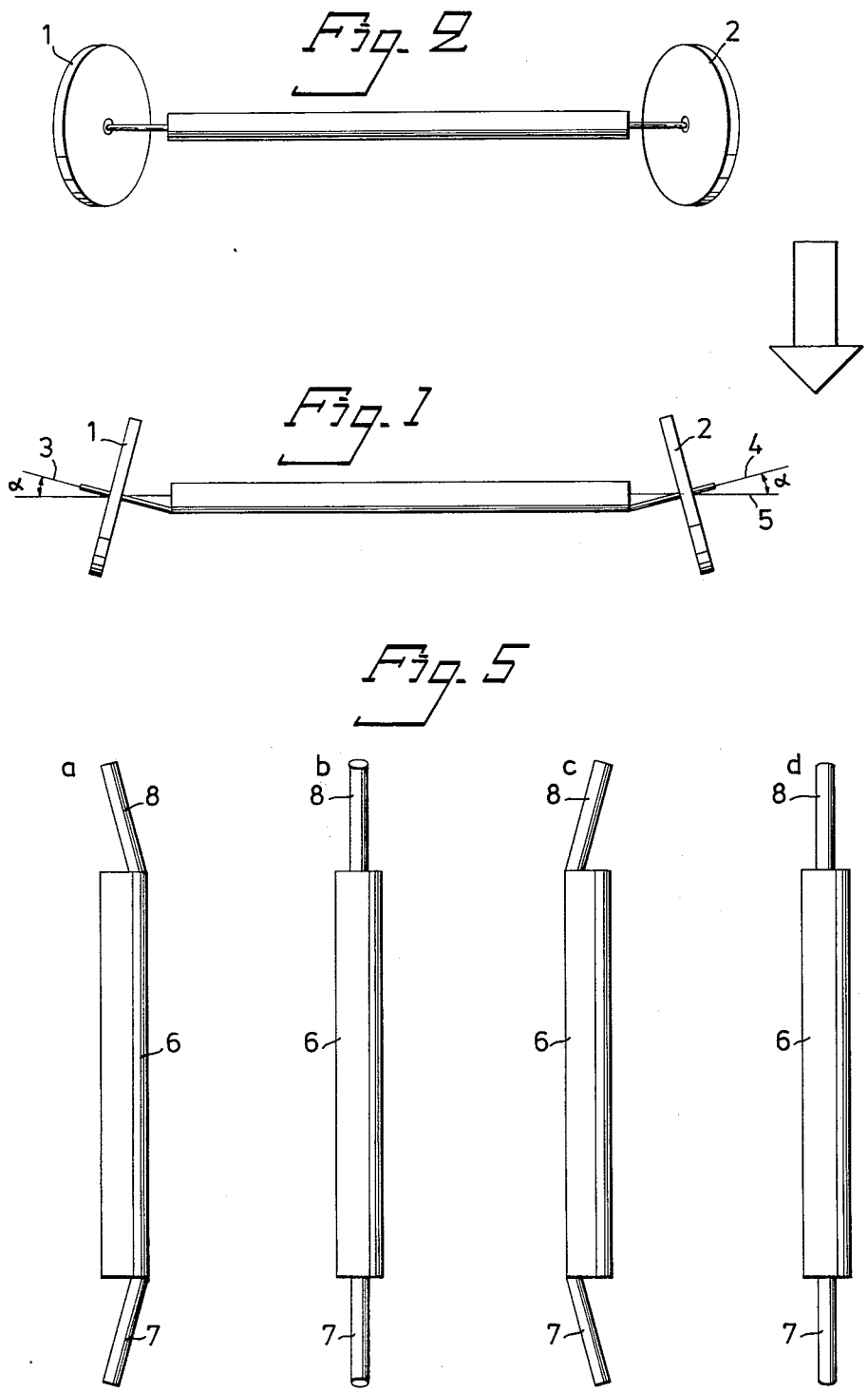

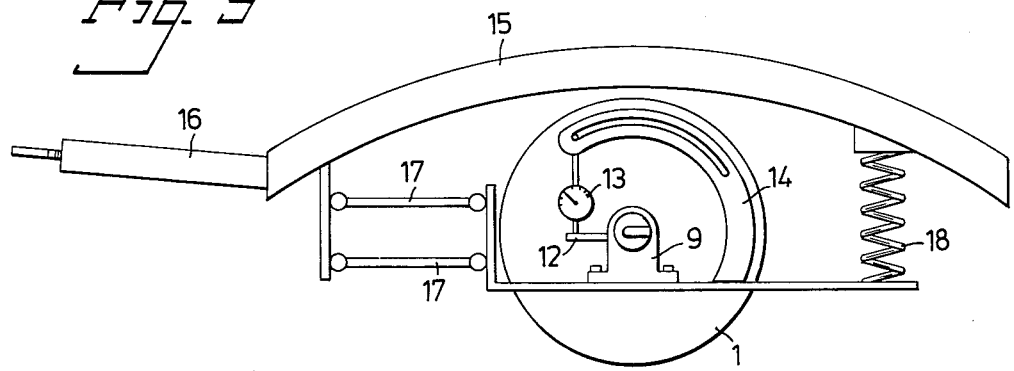
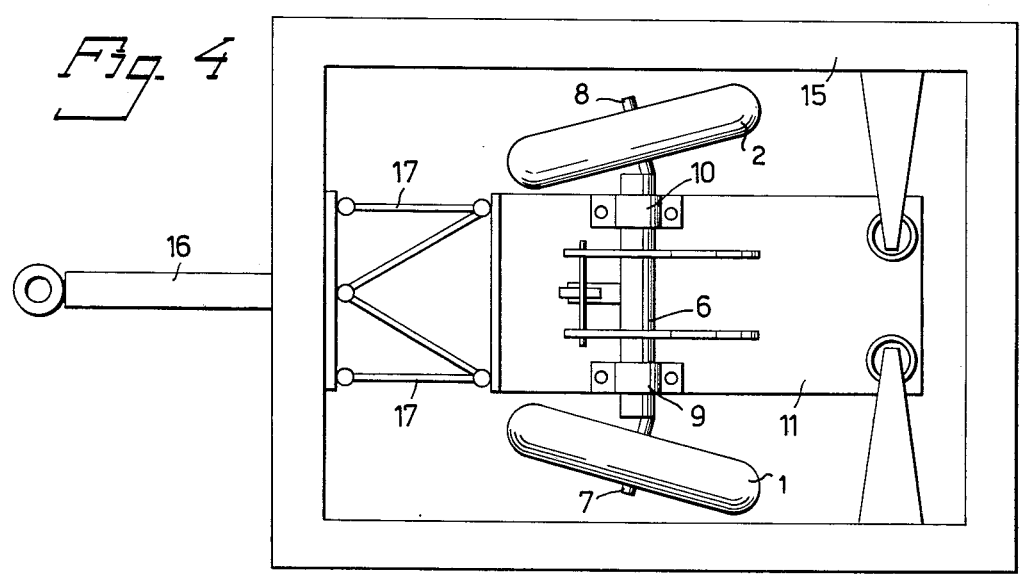

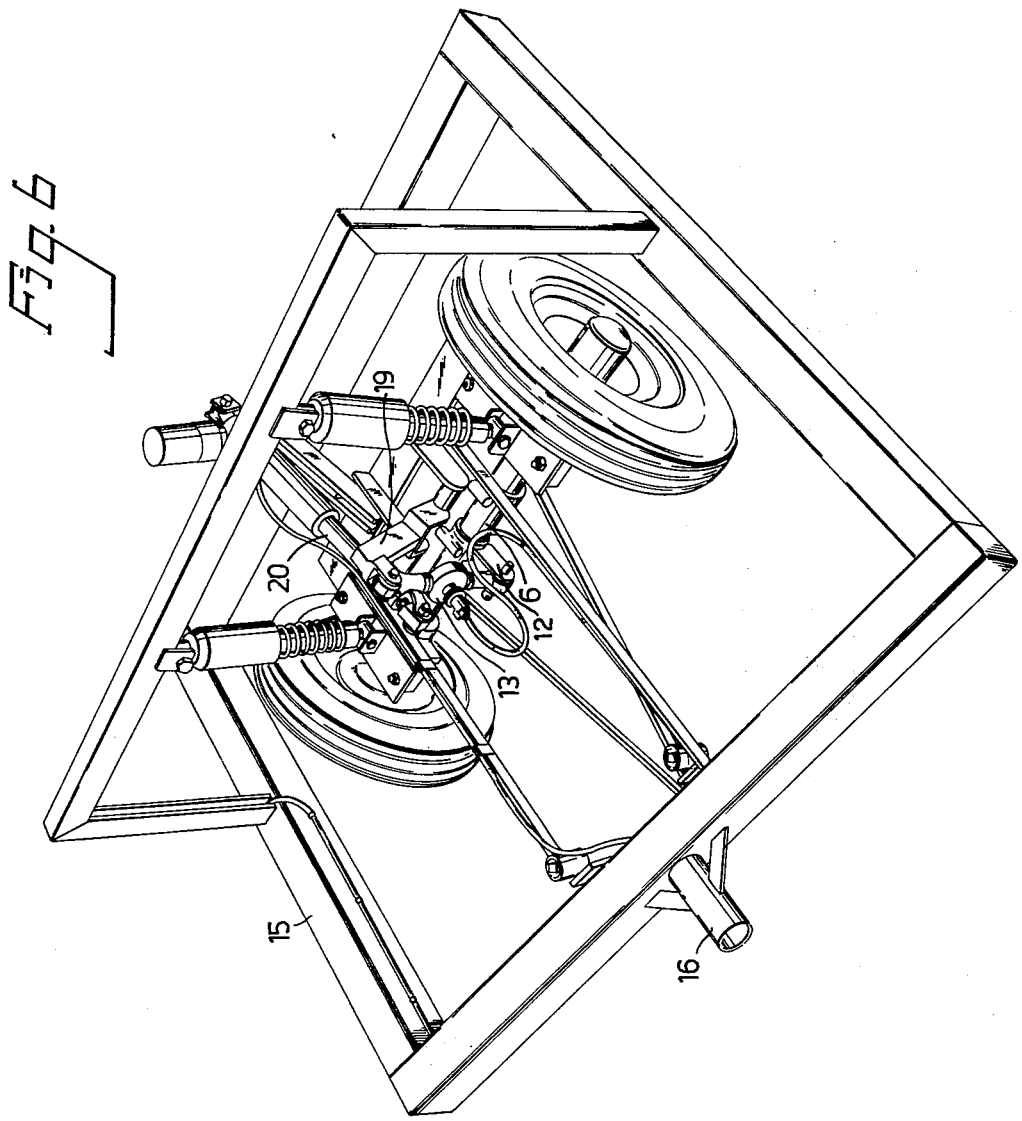

DEVICE FOR MEASURING FRICTION BETWEEN WHEEL AND SUPPORT

The present invention relates to a device for measuring friction between wheel and support, for example the paving on a road or runway for aircraft.

Utilizing conventional devices of the kind in question, forces produced by the friction between wheel and support are measured on one or several wheels being moved along the support. In order to obtain measurable forces, it has previously been known either to brake a wheel intermittently to locked position or by force to limit the rotation speed of a wheel so that its circumferential speed in a predetermined way falls below the speed of movement. According to another known device, one or two wheels of somewhat inclined position to the direction of movement are used, and the force required for maintaining the orientation of the wheel or wheels relative to the direction of movement is measured.

The present invention, like said lastmentioned device, is based on the movement of one or more wheels somewhat inclined to the direction of movement. As distinguished from previously known devices, however, a device according to the invention is designed so that the friction upon movement of the wheels results in a measurable turning moment about a line, which on the large is perpendicular to the direction of movement and substantially in parallel or coinciding with a line through the centers of the wheels. The moment arises and is measured on suspension means of the wheels and/or on a member interconnecting the same.

According to a preferred embodiment, the device according to the invention is designed so that the moment is substantially proportional to the friction.

According to a second preferred embodiment of the invention, the suspension of the wheels is so designed that the orientation of the rotation axis lines of the wheels can be varied synchronously between a transport position, at which said moment is substantially at minimum, and a measuring position, at which said moment is substantially at maximum.

According to a third embodiment, the device comprises two wheels, each suspended on an inclined axle journal of a carrying axle in a trailer vehicle, and the turning moment on the axle is measured.

Embodiments of the invention are discussed and described with reference to the drawings, in which details not essential for the understanding of the invention have been omitted for reason of clarity. The basic principle for a device with two wheels according to the invention is illustrated by FIGS. 1 and 2, while FIGS. 3 and 4 in a more complete manner show a preferred embodiment of a device according to the invention. FIG. 5 shows different positions of orientation for an axle with two inclined axle journals, and FIG. 6 shows an embodiment with turning means for turning such an axle between a transport position and a measuring position.

FIGS. 1 and 2 show from above and from the front, respectively, two wheels, 1 and 2, which are so suspended on an axle with inclined axle journals that each wheel can rotate about, but not be moved along its rotation axis line, 3 and 4, respectively. When the axle and wheels are moved with the wheels abutting to and rolling on a support in plane with the paper, with maintained orientation according to FIG. 1 in the direction of the arrow, then forces produced by the friction and the load on the wheels will arise in the contact surface between the support and the periphery of the wheels. It can be shown, by component division etc., that these forces generally cause both a turning moment on the axle and forces in the longitudinal and transverse direction of the axle.

When, for reason of simplicity, it is first assumed that the wheels are substantially equal, non-elastic and symmetric about the respective centre and rotation axis line, that the rotation axis lines form angles, $\alpha$, of equal size with a line 5, lying in the plane of the paper, and intersect said line in the centre of the respective wheel, and that the wheels carry a load of equal size and are moved perpendicularly to the line 5, the forces arising in the radial and axial direction of the axle substantially balance each other, and only a turning moment about the line 5 on the axle is obtained which is proportional to the load of the wheel and the friction force. The load being known, this moment can be used as a measure of the friction coefficient.

In practice, of course, it is not possible to design a device, to which all aforesaid symmetry conditions etc. apply. Elastic deformation and asymmetry of wheels, axles and axle journals as well as bearing friction etc. always give rise in practice to a greater or smaller deviation from an accurate proportional relation between turning moment and friction coefficient. It is, however, fully possible by suitable material choice, dimensioning and construction to obtain a measurable turning moment, which is a sufficiently accurate measure for practical use of the friction coefficient at the rolling of wheels on the support.

According to the laws of mechanics, a linear relation exists between the turning moment produced by a force about two parallel lines. The turning moment at a device according to FIGS. 1-2 need not necessarily be measured about the line 5, but can be measured about another line in parallel with the line 5, if for calculation-technical reasons a relation can be accepted which is only linear, instead of a directly proportional relation between moment and friction coefficient. This is essential for at least three reasons. Firstly, in practice the geometric centers of the wheels and a line through the same are not unambiguously well-defined magnitudes, because they vary with the wear and elastic deformation of the wheels. Secondly, the wheels can easily assume such a form, due to varying elastic deformation etc., that forces from the support on the wheels which are independent of the friction and, for example, caused by the weight with which the wheels rest on the support, in practice will exert a turning moment about the line 5. Then a linear but not proportional relation between the friction coefficient and the total turning moment about the line is obtained. Thirdly, for measuring-technical reasons it may be more suitable to measure the turning moment about a line other than that through the centers of the wheels.

For the movement of the wheels and axle in FIG. 1 with maintained orientation in the direction of the arrow along the support, several arrangements can be imagined. One alternative is to mount the axle behind the rear axle of a motor vehicle, for example a truck. The axle with wheels preferably is so arranged that it can be lifted and lowered, and the wheels abut the support only when measuring is to be carried out. It is wellknown to provide trucks with rearwardly located axles and wheels, which axles are liftable and lowerable so that the wheels on the axle rest on the road surface only when so is desired. It should, therefore, not be necessary to describe how the axle with wheels according to FIG. 1 can be mounted on a truck or the like. Instead, with reference to FIGS. 3-4 another alternative is described where the axle with wheels according to FIG. 1 has been mounted on a trailer vehicle.

FIGS. 3-4 show from the side and, respectively, from above a device according to the invention which is based on the basic principle illustrated in FIGS. 1-2. The device comprises two wheels, 1 and 2, each suspended on an axle journal, 7 and 8, respectively, of a carrying axle 6. As is most clearly apparent from FIG. 4, the axle journals are somewhat inclined in relation to the carrying axle and so located and oriented that their centre lines lie substantially in the same plane and intersect the center line of the carrying axle so as to form angles a of substantially equal size. These angles are of the order of magnitude 6°-8°, but are exaggerated in the Figures for reason of better clearness. The carrying axle is mounted in bearing means, 9 and 10, for supporting a structure 11, which is not spring-suspended. For measuring the turning moment on the carrying axle about its centre line, the axle is provided with a projection or a lever 12, and the nonspring suspended structure is provided with a dynamometer 13 disposed in a suspension means 14. A spring-suspended load 15 with drawbar 16 is connected with the nonspring suspended structure via tie rods 17 and substantially vertically arranged springs 18. At friction measuring, the device according to FIGS. 3-4 is coupled with the drawbar to a traction vehicle and moved to the left along, for example, a car road or a runway for aircraft. The wheels, thus, are arranged toe-in relative to the movement direction according to FIGS. 3-4, but can within the scope of the invention instead be arranged toe-out according to FIGS. 1-2.

A great number of variations of the described device according to FIGS. 3-4 are possible within the scope of the invention. The symmetry conditions discussed in connection with FIGS. 1-2, of course, need not be met accurately, and particularly the rotation axis lines of the wheels must not necessarily lie in accurately the same plane of intersect the line through the centers of the wheels to form angles of accurately equal size. The angle need not be 6°-8°, but can be of any size between about 2° and about 20°, depending on the wheels, support and application field of the device.

The measuring of the turning moment, of course, can take place in another way than by measuring a force proportional thereto according to FIGS. 3-4. When a substantially directly proportional relation between the turning moment about a line and the friction coefficient is desired, the position of the wheels along the rotation axis lines must be chosen so that forces independent of the friction, for example normal forces of the wheels from the support counteracting the weight of the device, together do not exert an appreciable turning moment about the line. This implies, at the use of elastically deformable wheels and/or wheels which do not comply with the symmetry assumptions in a device according to FIGS. 3-4, that the center line of the carrying axle need not intersect the rotation axis lines of the wheels accurately in the centers of the wheels.

In order to explain the basic principle for an embodiment of the invention, in FIG. 1 a wheel suspension means in the form of an axle with two inclined axle journals is used. In a device according to the present invention, however, it is not absolutely necessary that two wheels must be suspended each on an axle journal of a common axle according to FIGS. 1-2. The number of wheels used to produce a turning moment may be higher or lower than two, and when two wheels are used, other suspension means may be used. The essential feature is that the suspension means are such that the wheels each can rotate about, but not be moved along its rotation axis line, and with maintained orientation according to FIG. 1 or 4 or 5 can be moved along the support and transfer a measurable turning moment about a line substantially perpendicularly to the direction of movement and substantially in parallel with the support. Instead of one axle with two inclined axle journals it would be possible for a device in general according to FIGS. 3-4 to have two parallel axles each with one inclined axle journal. In that case, of course, the mounting (details 9 and 10) of the axles must be completed to receive forces in the longitudinal and transverse direction of the axles without appreciably affecting the turning moments to be measured. When the suspension means of the wheels are not rigidly connected to each other, instead of one common measuring device for the turning moment according to FIGS. 3-4 two measuring devices may be provided with each separately measure the turning moment on the respective wheel suspension means, whereafter the measuring results are added.

The discussion so far has only dealt with devices having two wheels. According to an imaginable embodiment of the invention only one wheel is used which is suspended on an inclined axle journal on an axle, i.e. substantially half of the device shown in FIGS. 1-2. Such a device could be positioned with the wheel in a rear axle line of a motor vehicle and be located either between the rear wheels or outside of one of the rear wheels. Also in this case, of course, the mounting of the axle must be designed so as to receive forces in the longitudinal and transverse direction of the axle without appreciably affecting the turning moment to be measured.

It is possible in principle to use more than two wheels, for example four, in order to produce a turning moment for friction measuring, but the embodiments which for several reasons are to be preferred are based on two wheels and one suspension means comprising one axle with two inclined axle journals.

Irrespective of the number of wheels, which according to the invention are used to produce a turning moment about a line substantially perpendicular to the direction of movement and in parallel with the support, the device according to a preferred embodiment is provided with a means for turning the rotation axis direction for each wheel between one or more measuring positions and one or more transport positions. For a device based on one axle with two inclined axle journals, FIGS. 2 and 5c show measuring positions with toe-out, and FIGS. 4 and 5a show measuring positions with toe-in, while FIG. 5b shows a transport position with negative camber angle, and FIG. 5d shows a transport position with positive camber angle. It lies, of course, within the scope of the invention, irrespective of the number of wheels used for producing the measurable turning moment, to use also other orientation positions for the respective rotation axis direction in relation to the direction of movement than those shown in FIGS. 1-5. The shown orientation positions, however, are to be preferred as they render maximum moment at measuring and minimum moment at transport. One advantage of the possibility of turning between different measuring positions and transport positions is that the wear of the wheels to a substantial part can be shifted between different portions of the tread of the wheels at measuring, and that the wear can be reduced substantially at transport.

FIG. 6 shows an embodiment comprising a means for synchronously turning the rotation axis lines for two wheels where the wheel suspension means comprises an axle with two inclined axle journals according to FIGS. 1-5. An extensive description of the Figures should not be necessary, but it should be sufficient to point out that the stationary suspension means 14 in FIGS. 3-4 has been replaced by a movable suspension means for the dynamometer 13. When the position for the suspension means 19 is changed by the hydraulic means 20, the movement of the dynamometer 13 is transferred via the projection 12 to the axle 6.

When at friction measuring according to the invention a number of wheels other than two or a wheel suspension means other than one axle with two inclined axle journals are used, the means for turning the rotation axis directions, of course, must be adapted thereto. The specific design for this turning means is now, however, essential for the present invention. The main feature is that the rotation axis directions are turned synchronously when more than one wheel is used for producing the measurable turning moment.

Although the above invention has been defined in a very specific and illustrative manner, any suitable equivalent substitution may be made without deviating from the present invention. Thus, anyone skilled in the art may have other modifications which they may make to carry out the spirit of the present invention. These modifications and substitutions are intended to be encompassed within the scope of the present invention.

It is claimed:

1. A device for measuring friction between wheel and support comprising:
   a. at least one wheel with a wheel suspension means permitting the wheel to rotate about a rotation axis line;
   b. means for moving the wheel suspension means with the wheel rolling on the support and somewhat inclined to the direction of movement; and
   c. measuring means for measuring the turning moment about a line being on the whole horizontal and substantially perpendicular to the direction of movement, which moment is produced on the wheel suspension means by the forces arising at the movement in the contact surface between the wheel and support.

2. A device according to claim 1, wherein the wheel suspension means is provided with a portion for measuring the turning moment, said portion being turnable about the measuring line.

3. A device for measuring friction between wheel and support comprising:
   a. two wheels with a wheel suspension means permitting the wheels to rotate each about a rotation axis line, which lines form with the direction for a line through the centers of the wheels angles of substantially equal size;
   b. means for moving the wheel suspension means in a direction substantially perpendicular to the line through the centers of the wheels, the wheels rolling on the support and somewhat inclined to the direction of movement; and
   c. measuring means for measuring the turning moment about a measuring line coinciding or in parallel with said line through the centers of the wheels, which moment is produced on the suspension means of the wheels by the force arising at the movement in the contact surfaces between the wheels and the support.

4. A device according to claim 3, where the wheel suspension means has a portion turnable about the measuring line, on which portion the turning moment is measured.

5. A device according to claim 4, wherein the measuring line substantially intersects the rotation axis lines in the vicinity of the centers of the wheels, whereby normal forces from the support on the wheels counteracting the weight of the device together do not exert any turning moment of importance upon the measuring line.

6. A device for measuring friction between wheel and support comprising:
   a. wheel suspension means comprising an axle with two inclined axle journals;
   b. a first wheel suspended on one of said axle journals to rotate about a first rotation axis line;
   c. a second wheel suspended on the other of said axle journals to rotate about a second rotation axis line, said first and second rotation axis lines lying substantially in the same plane and forming with the direction for a line through the centers of the wheels angles of substantially equal size;
   d. means for moving the wheel suspension means in a direction substantially perpendicular to said line through the centers of said wheels, the wheels rolling on the support and somewhat inclined to the direction of movement, whereby the forces arising at the movement in the contact surfaces between the wheels and support produces a turning moment on said axle about a measuring line in parallel with said line through the centers of said wheels; and
   e. measuring means for measuring said moment on said axle about said measuring line.

7. A device according to claim 6, further including turning means for turning said axle and axle journals about said measuring line.

8. A device according to claim 7, wherein the measuring line substantially intersects the rotation axis lines in the vicinity of the centers of the wheels, whereby normal forces from the support on the wheels counteracting the weight of the device together do not exert any turning moment of importance upon the measuring line.

* * * * *

UNITED STATES PATENT AND TRADEMARK OFFICE
CERTIFICATE OF CORRECTION

PATENT NO. : 4,050,290
DATED : September 27, 1977
INVENTOR(S) : Borje Arne Gunnar Lonnroth It is certified that error appears in the above—identified patent and that said Letters Patent are hereby corrected as shown below:

UNDER THE HEADING

"[30] Foreign Application Priority Data" add the following:

--February 25, 1975 Sweden 7600403--

*Signed and Sealed this*

*Eleventh* Day of *April 1978*

[SEAL]

Attest:

RUTH C. MASON
*Attesting Officer*

LUTRELLE F. PARKER
*Acting Commissioner of Patents and Trademarks*